(12) United States Patent
Scialdone et al.

(10) Patent No.: US 7,776,912 B2
(45) Date of Patent: Aug. 17, 2010

(54) ACETALS OF NEPETALIC ACID AND METHOD OF PREPARATION

(75) Inventors: Mark A. Scialdone, West Chester, PA (US); Ann Y. Liauw, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 476 days.

(21) Appl. No.: 11/769,101

(22) Filed: Jun. 27, 2007

(65) Prior Publication Data

US 2009/0087387 A1 Apr. 2, 2009

Related U.S. Application Data

(60) Provisional application No. 60/818,124, filed on Jun. 30, 2006.

(51) Int. Cl.
*A01N 43/16* (2006.01)
*A01N 37/08* (2006.01)
*C07D 311/94* (2006.01)
*C07C 69/757* (2006.01)

(52) U.S. Cl. .................. 514/456; 514/530; 549/285; 560/122

(58) Field of Classification Search .............. 549/285; 560/122; 514/456, 530
See application file for complete search history.

(56) References Cited

U.S. PATENT DOCUMENTS

| 6,524,605 B1 | 2/2003 | Coats et al. |
| 7,435,851 B2 | 10/2008 | Scialdone |
| 2003/0062357 A1 | 4/2003 | Schneider et al. |
| 2003/0079786 A1 | 5/2003 | Diana et al. |
| 2003/0191047 A1 | 10/2003 | Hallahan |
| 2003/0235601 A1 | 12/2003 | Hallahan |
| 2005/0137252 A1 | 6/2005 | Scialdone |

FOREIGN PATENT DOCUMENTS

| WO | WO 03/079786 A1 | 10/2003 |
| WO | WO 2005/054224 A2 | 6/2005 |
| WO | WO 2006/072037 | 7/2006 |
| WO | WO 2006/072039 | 7/2006 |
| WO | WO 2007/041306 | 4/2007 |

OTHER PUBLICATIONS

U.S. Appl. No. 60/818,124, filed Jun. 30, 2006, Mark A. Scialdone et al.
T. Eisner et al., Catnip: Its Raison D'Etre, Science, 1964, vol. 146:1318-1320.
Jefson et al., Chemical Defense of a Rove Beetle, Journal of Chemical Ecology, 1983, vol. 9:159-180.
Dawson et al., The Aphid Sex Pheromone Cyclopentanoids: Synthesis in the Elucidation of Structure and Biosynthetic Pathways, Bioorganic & Medicinal Chemistry, 1996, vol. 4:351-361.
Greene et al., Acetals and Ketals, Protecting Groups in Organic Synthesis, 1991, pp. 178-183, John Wiley & Sons.
Eisenbraun et al., Structure of Nepetalic Acid in the Solid State and in Solution by X-ray Diffraction and Nuclear Magnetic Resonance Analysis, J. Org. Chem., 1981, vol. 46:3302-3305.
Chauhan et al., Iridodials: Enantiospecific and Stereochemical Assignment of the Pheromone for the Golden-Eyed Lacewing, *Chrysopa Oculata*, Tetrahedron Letters, 2004, vol. 45:3339-3340.
International Search Report Dated Jan. 11, 2008, International Application No. PCT/US2007/015324, International Filing Date: Jun. 29, 2007.
U.S. Appl. No. 12/107,863, filed Apr. 23, 2008, Scialdone.

*Primary Examiner*—Bernard Dentz

(57) ABSTRACT

Disclosed are acetals of nepetalic acid. They may be prepared by reaction of an alcohol with nepetalic acid, and are useful as repellents for insects and arthropods, in addition to other uses.

20 Claims, No Drawings

ACETALS OF NEPETALIC ACID AND METHOD OF PREPARATION

This application claims the benefit of U.S. Provisional Application No. 60/818,124, filed Jun. 30, 2006, which is incorporated in its entirety as a part hereof for all purposes.

TECHNICAL FIELD

This invention is directed to acetals of nepetalic acid, which are useful as repellents for insects and arthropods.

BACKGROUND

Insect repellents are used globally as a means of reducing human-insect vector contact, thereby minimizing the incidence of vector-borne disease transmission as well as the general discomfort associated with insect bites. The best known and most widely used active ingredient in commercial topical insect repellents is the synthetic benzene derivative, N,N-diethyltoluamide (DEET).

Nepetalactone (represented in general by schematic Formula X),

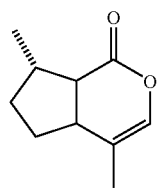

X is a major component of an essential oil secreted by plants of the genus *Nepeta* and the active ingredient in catnip, and is known to be an effective, natural repellent to a variety of insects [Eisner, T., *Science* (1964) 146:1318-1320]. U.S. Pat. No. 6,524,605 discloses the repellency of nepetalactone, as well as the individual cis,trans (Z,E) and trans,cis (E,Z) isomers, against German cockroaches.

Dihydronepetalactone (DHN), represented in general by schematic Formula I,

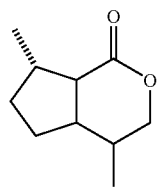

I is a chemical which is secreted by certain insects, and is known to exhibit insect repellency activity. Jefson et al [*J. Chemical Ecology* (1983) 9:159-180] described the repellent effect of DHN on feeding by ants of the species *Monomorium destructor*. More recently, Hallahan (WO 03/79786) has found that DHN compares favorably as an insect repellent with DEET.

Dawson et al have described a method of preparing the ethyl acetal of nepetalic acid from carvone in a seven step procedure as set forth in "The Aphid Sex Pheromone Cyclopentanoids Synthesis in the Elucidation of Structure and Biosynthetic Pathways" in *Bioorganic & Medicinal Chemistry* 4(3): 351-361 (1996) as shown below in Table 1. The compounds made by this process have the R configuration at the methyl-bearing carbon on the cyclopentyl ring.

TABLE 1

Synthesis of ethyl acetal of nepetalic acid

Scheme 1

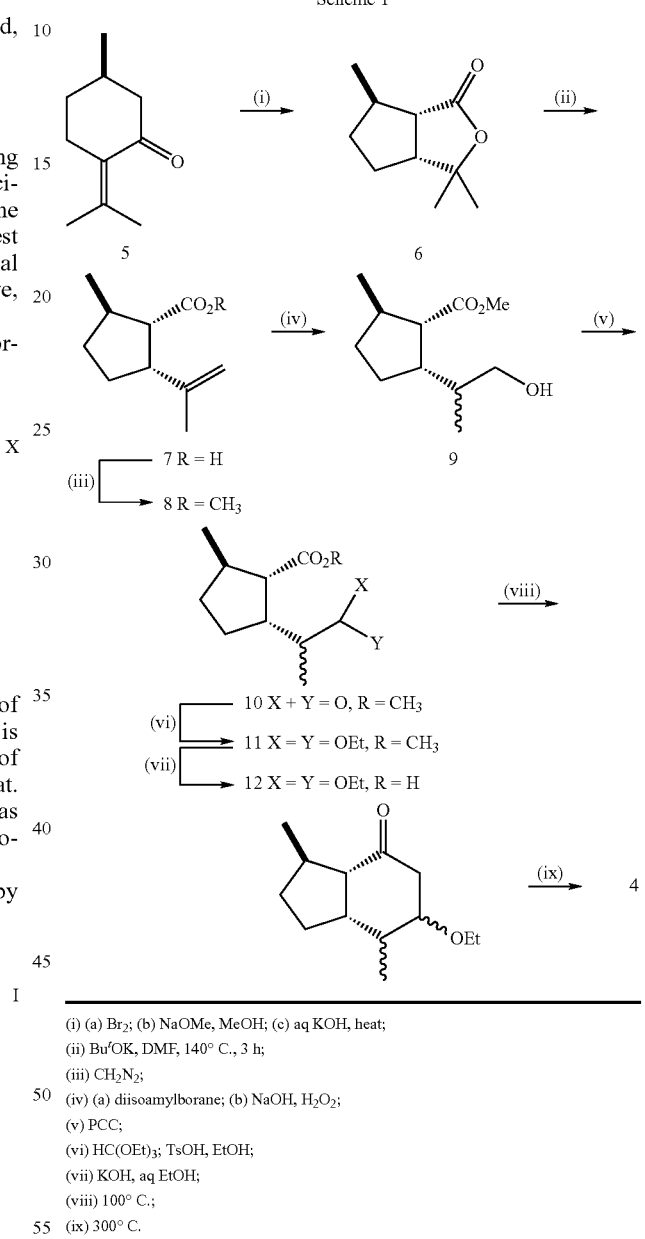

(i) (a) Br$_2$; (b) NaOMe, MeOH; (c) aq KOH, heat;
(ii) Bu$^t$OK, DMF, 140° C., 3 h;
(iii) CH$_2$N$_2$;
(iv) (a) diisoamylborane; (b) NaOH, H$_2$O$_2$;
(v) PCC;
(vi) HC(OEt)$_3$; TsOH, EtOH;
(vii) KOH, aq EtOH;
(viii) 100° C.;
(ix) 300° C.

Despite the previous work as described above, a need remains for the continued availability of as wide a variety of insect repellents as possible, and the novel acetals described herein have been found to be useful as repellents for insects and arthropods, as well as for other purposes.

SUMMARY

In one embodiment, this invention provides a compound represented in general by the following schematic formula:

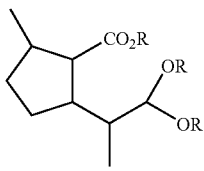

wherein R comprises (a) an alkane radical, (b) an alkene radical, (c) an alkyne radical, or (d) an aromatic radical. In various embodiments, the compound is S configured at the methyl-bearing carbon on the cyclopentyl ring.

In another embodiment, this invention provides a compound represented in general by the by the following schematic formula:

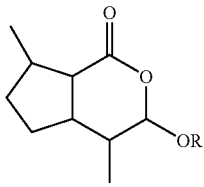

wherein R comprises (a) an alkane radical, (b) an alkene radical, (c) an alkyne radical, or (d) an aromatic radical. In various embodiments, the compound is S configured at the methyl-bearing carbon on the cyclopentyl ring.

In yet another embodiment, this invention provides a composition of matter that includes (a) one or more compounds as described above, and (b) a carrier to adjust the concentration of the compound within the composition, and/or a cosmetic adjuvant.

In yet another embodiment, this invention provides a process for preparing a nepetalic acid acetal comprising contacting a nepetalic acid with an alcohol.

In yet another embodiment, this invention provides a method for repelling an insect or arthropod comprising exposing the insect or arthropod to one or more compounds as described above, or a composition thereof.

Yet another embodiment of this invention is the use of one or more compounds as described above, or a composition thereof, to repel insects and/or arthropods from a human, animal or inanimate host for same.

Yet another embodiment of this invention is an article of manufacture that incorporates one or more compounds as described above.

Yet another embodiment of this invention is a method of fabricating an insect repellent composition, or an insect repellent article of manufacture, by forming the composition from, or incorporating into the article, one or more compounds as described above.

Yet another embodiment of this invention is a method of fabricating a composition to be applied to skin, or a fragrant article of manufacture, by forming the composition from, or incorporating into the article, one or more compounds as described above. The composition to be applied to skin is applied thereto for the purpose of imparting a fragrance or therapeutic effects to skin.

DETAILED DESCRIPTION

The present invention relates to novel compounds that are acetals of nepetalic acid, and to compositions of those compounds, and methods of preparation such compounds. These compounds are useful as repellents against ticks and insects, and for other personal care purposes.

An acetal is a common derivative of an aldehyde. A typical method for its preparation from an aldehyde with an alcohol is shown generally in the reaction scheme described in Equation 1, and is more extensively described in *Protecting Groups in Organic Synthesis* (Greene et al, John Wiley & Sons, New York, 1991, pages 178-183). As noted in Equation 1, the presence of an acid catalyst is typically required to obtain a usefully effective reaction.

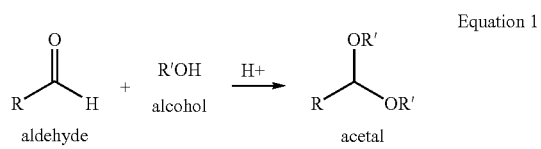

Equation 1

As shown in Equation 2, a lactol is a cyclic tautomer of a hydroxy-aldehyde, and it may also be reacted with an alcohol to form an acetal, as indicated generally by the reaction scheme described by Equation 2. A lactol has enhanced reactivity compared to an aldehyde in this type of acetalization reaction. No acid catalyst is typically required to obtain a usefully effective reaction with an alcohol because of the relative stability of the acetal over the lactol, which is a hemiacetal.

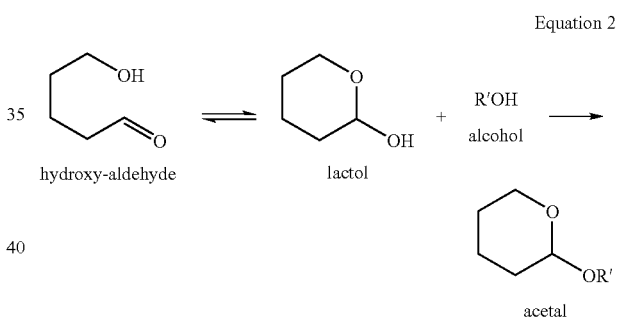

Equation 2

The acetal compounds represented generally below by schematic Formulae V and VI may be prepared by a process of the invention, which is the acetalization of a nepetalic acid with an alcohol. In one embodiment, nepetalic acid for use as a precursor material in a process hereof may be prepared from nepetalactone in a hydration reaction, which is summarized generally in the reaction scheme described in Equation 3. A nepetalic acid suitable for use as a precursor material in a process hereof is represented generally by both schematic Formula VII and schematic Formula VIII as shown in Equation 3.

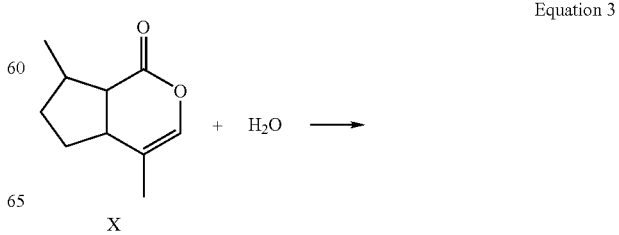

Equation 3

When a nepetalic acid precursor material for use in an acetalization reaction hereof is prepared from nepetalactone, the nepetalactone may be extracted from the essential oil of leaves of the *Nepeta cateria* (catmint) plant. Nepetalactone is present in large quantity therein, and the essential oil obtained by pressing or steam distilling the plant material contains several different stereoisomers of nepetalactone. Fractional distillation has been found to be an effective method for both purifying the nepetalactone as obtained from the essential oils, and for separating the several stereoisomers from one another. Chromatographic separations are also suitable. This produces a desirable route from a natural product to the compounds of the invention.

Among the various stereoisomers of nepetalactone obtained from the essential oil of the catmint plant, those shown generally below by schematic Formulae X(a) to X(d) are obtained in relative abundance, particularly the cis,trans and trans,cis stereoisomers [Formulae X(a) and X(b)]. Correspondingly, when neptalactone is used to make nepetalic acid, although all nepetalactone isomers present participate in the hydration reaction, the nepetalic acid products of the cis,trans and trans,cis isomers of nepetalactone are frequently the most readily identified and recovered among them. The isomers of nepetalactone obtained from catmint oil have the S configuration at the methyl-bearing carbon on the cyclopentyl ring, and nepetalic acid made therefrom does as well.

In one embodiment of the process hereof, a nepetalic acid acetal is prepared by contacting a nepetalic acid with an alcohol.

When a nepetalic acid that exists, for example, in the form of a cyclic lactol tautomer (as represented generally by schematic Formula VII) is used to prepare an acetal, the reaction may proceed generally according to the reaction scheme depicted by Equation 4, and the product acetal may be described generally by schematic Formula V. The cyclic lactol tautomer as represented generally by schematic Formula VII may be derived by hydration, for example, from cis,trans-nepetalactone as shown in Formula X(a).

The type of reaction involving the use of a cyclic lactol tautomer as shown in Equation 4 is essentially instantaneous, and it happens upon dissolving the nepetalic acid in the requisite alcohol, as verified by NMR analysis. The reaction typically requires no catalyst.

When a nepetalic acid that exists, for example, in the form of a ring-opened carboxy-aldehyde tautomer (as represented generally by schematic Formula VIII) is used to prepare an acetal, the reaction may proceed under acidic conditions generally according to the reaction scheme depicted by Equation 5, and the product acetal may be generally described by schematic Formula VI. The ring-opened carboxy-aldehyde tautomer as represented generally by schematic Formula VIII may be derived by hydration, for example, from trans,cis-nepetalactone as shown in Formula X(b).

Equation 5

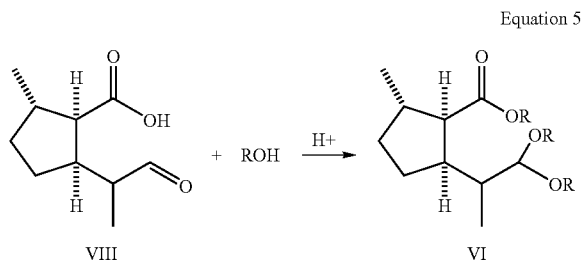

Under these reaction conditions, esterification of the free carboxylic acid with the alcohol used also occurs, which results in ester-acetal isomers as represented generally by schematic Formula VI.

Suitable alcohols for use in any type of reaction for the acetalization of a nepetalic acid include those in which the R group in R—OH is derived from (a) an alkane radical (such as a $C_1$ to $C_{20}$ alkane radical), (b) an alkene radical (such as a $C_2$ to $C_{20}$ alkene radical), (c) an alkyne radical (such as a $C_2$ to $C_{20}$ alkyne radical), or (d) an aromatic radical (such as a $C_6$ to $C_{20}$ aromatic radical). The term "alkane" in this context refers to a saturated hydrocarbon having the general formula $C_nH_{2n+2}$. The term "alkene" refers to an unsaturated hydrocarbon that contains one or more C=C double bonds, and the term "alkyne" refers to an unsaturated hydrocarbon that contains one or more carbon-carbon triple bonds. An alkene or alkyne requires a minimum of two carbons. A cyclic compound requires a minimum of three carbons. The term "aromatic" refers to benzene and compounds that resemble benzene in chemical behavior.

Suitable alcohols may include those in which the R group in R—OH is derived, for example, from a $C_1$ to $C_{20}$, $C_1$ to $C_{12}$, $C_1$ to $C_8$, $C_3$ to $C_{20}$, $C_3$ to $C_{12}$ or $C_3$ to $C_8$ straight-chain, branched or cyclic alkane or alkene radical; any of which radicals may include one or more heteroatoms selected from the group consisting of O, N and S, and/or may also include a substituent derived from a $C_6$ to $C_{20}$ aromatic radical.

Suitable alcohols may also include those in which the R group in R—OH is derived, for example, from an unsubstituted or substituted $C_6$ to $C_{20}$ aromatic radical, wherein a substituent thereon is selected from the group consisting of (a) $C_1$ to $C_{12}$ straight-chain, branched or cyclic alkane or alkene radical, optionally substituted with Cl, Br or F, and (b) a halogen selected from the group consisting of Cl, Br and F. Any of these unsubstituted or substituted $C_6$ to $C_{20}$ aromatic radicals may optionally also include one or more heteroatoms selected from the group consisting of O, N and S.

In other embodiments, values for R may include any one or more of methyl, ethyl, n-propyl, i-propyl, n-butyl, t-butyl, n-pentyl, n-hexyl, cyclohexyl, n-octyl, trimethylpentyl, cyclooctyl, allyl, propargyl, phenyl, methylphenyl, ethylphenyl, n-propylphenyl, n-butylphenyl, t-butylphenyl, p-chlorophenyl, p-bromophenyl, naphthyl and ethyl naphthyl. In certain other embodiments, however, ethyl may be excluded as a value for R.

The nepetalactone, nepetalic acid and acetal compounds described herein will be recognized as exhibiting stereoisomerism, both enantiomerism and diastereomerism, as the case may be. Unless a specific stereoisomer is indicated, the discussion will be understood to refer to all possible isomers, whether a structure is shown in the stereochemically ambiguous form of the structure of Formula I, or is shown as a specific stereoisomer (as, for example, in Formulae V to VIII) when other stereoisomers are also possible. As a result, a compound according to this invention includes a compound that is a single stereoisomer as well as a compound that is a mixture of stereoisomers where R is the same in each stereoisomer. But in this invention, a composition may also be formed from a mixture of the compounds of this invention in which R, as described above, differs among the various compounds from which the composition is formed. In certain specific embodiments of this invention, an acetal will have the S configuration at the methyl-bearing carbon on the cyclopentyl ring, which is C-7 according to the numbering scheme for nepetalactone as shown below in Formula X:

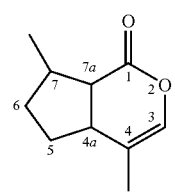

The acetal compounds of this invention may be used individually or together for a multiplicity of purposes, such as use as an active in an effective amount for the repellency of various insect or arthropod species, or as a fragrance compound in a perfume composition, or as a topical treatment for skin. For example, these compounds may be applied in a topical manner to the skin, hide, hair, fur or feathers of a human or animal host for an insect or arthropod, or to an inanimate host such as growing plants or crops, to impart insect or arthropod repellency or a pleasant odor or aroma. An inanimate host may also include any article of manufacture that is affected by insects, such as buildings, furniture, containers, packaging materials, and the like. Typically, these articles of are considered to be insect-acceptable food sources or insect-acceptable habitats.

A repellent or repellent composition refers to a compound or composition that drives insects or arthropods away from their preferred hosts or from insect-suitable articles of manufacture or habitats. Most known repellents are not active poisons, but rather prevent damage to humans, animals plants and/or articles of manufacture by making insect/arthropod food sources or living conditions unattractive or offensive. Typically, a repellent is a compound or composition that can be topically applied to a host, or can be incorporated into an insect susceptible article, to deter insects/arthropods from approaching or remaining in the nearby 3-dimensional space in which the host or article exists. In either case, the effect of the repellent is to drive the insects/arthropods away from, or to reject, (1) the host, thereby minimizing the frequency of "bites" to the host, or (2) the article, thereby protecting the article from insect damage. Repellents may be in the form of gases (olfactory), liquids, or solids (gustatory).

One property that is important to overall repellent effectiveness is surface activity, as many repellents contain both polar and non-polar regions in their structure. A second property is volatility. Repellents form an unusual class of compounds where evaporation of the active ingredient from the host's skin surface, or from an insect-repellent article, makes an important contribution to its effectiveness, as measured by the protection of the host from bites or the protection of the article from damage.

In the case of a topical insect/arthropod repellent applied to the skin, hide, hair, feathers or fur of a host, one measure of the potency of the repellent is the extent to which the concentration of the repellent in the air space directly above the surface where applied is sufficient to repel the insects/arthropods. A desirable level of concentration of the repellent is obtained in the air space primarily from evaporation, but the rate of evaporation is affected by the rate absorption into the skin or other surface, and penetration into and through the surface is thus almost always an undesirable mode of loss of repellent from the surface. Similar considerations apply to articles that contain a repellent, or into which a repellent has been incorporated, as a minimum concentration of repellent in the three-dimensional air space surrounding the article itself favors achievement of the desired level of protection.

In selecting a substance for use as an insect/arthropod repellent active, the inherent volatility is thus an important consideration. A variety of strategies are available, however, when needed for the purpose of attempting to increase persistence of the active while not decreasing, and preferably increasing, volatility. For example, the active can be formulated with polymers and inert ingredients to increase persistence on a surface to which applied or within an article. The presence of inert ingredients in the formulation, however, dilutes the active in the formulation as applied, and the loss from undesirably rapid evaporation must thus be balanced against the risk of simply applying too little active to be effective. Alternatively, the active ingredient may be contained in microcapsules to control the rate of loss from a surface or an article; a precursor molecule, which slowly disintegrates on a surface or in an article, may be used to control the rate of release the active ingredient; or a synergist may be used to continually stimulate the evaporation of the active from the composition.

The release of the active ingredient may be accomplished, for example, by sub-micron encapsulation, in which the active ingredient is encapsulated (surrounded) within a skin nourishing protein similar to the manner in which air is captured within a balloon. The protein may be used, for example, at about a 20 wt % concentration to the weight of the total formulation. An application of repellent contains many of these protein capsules that are suspended in either a water-based lotion, or water for spray application. After contact with skin, the protein capsules begin to breakdown releasing the encapsulated active. The process continues as each microscopic capsule is depleted then replaced in succession by new capsules that contact the skin and release the active ingredient. The process may take up to 24 hours for one application. Because a protein adheres very effectively to skin, these formulations are very resistant to perspiration (sweat-off) and water from other sources.

One of the distinct advantages of the acetal compounds of this invention is that they are all characterized by a relative volatility that makes them suitable for use to obtain a desirably high level of concentration of active on, above and around a surface or article, as described above. One or more of these acetal compounds are typically used for such purposes as an active in a composition in which the compounds are admixed with a carrier suitable for wet or dry application of the composition to any surface in the form, for example, of a liquid, aerosol, gel, aerogel, foam or powder (such as a sprayable powder or a dusting powder). Suitable carriers include any one of a variety of commercially available organic and inorganic liquid, solid, or semi-solid carriers or carrier formulations usable in formulating skin or insect repellent products, and as such may be used to adjust the concentration with a composition or formulation of one or more acetal compounds therein. When formulating a skin product or topical insect repellent, it is preferred to select a dermatologically acceptable carrier. For example the carrier may include water, alcohol, silicone, petrolatum, lanolin or many of several other well known carrier components. Examples of organic liquid carriers include liquid aliphatic hydrocarbons (e.g. pentane, hexane, heptane, nonane, decane and their analogs) and liquid aromatic hydrocarbons.

Examples of other liquid hydrocarbons include oils produced by the distillation of coal and the distillation of various types and grades of petrochemical stocks, including kerosene oils that are obtained by fractional distillation of petroleum. Other petroleum oils include those generally referred to as agricultural spray oils (e.g. the so-called light and medium spray oils, consisting of middle fractions in the distillation of petroleum and which are only slightly volatile). Such oils are usually highly refined and may contain only minute amounts of unsaturated compounds. Such oils, moreover, are generally paraffin oils and accordingly can be emulsified with water and an emulsifier, diluted to lower concentrations, and used as sprays. Tall oils, obtained from sulfate digestion of wood pulp, like the paraffin oils, can similarly be used. Other organic liquid carriers can include liquid terpene hydrocarbons and terpene alcohols such as alpha-pinene, dipentene, terpineol, and the like.

Other carriers include silicone, petrolatum, lanolin, liquid hydrocarbons, agricultural spray oils, paraffin oil, tall oils, liquid terpene hydrocarbons and terpene alcohols, aliphatic and aromatic alcohols, esters, aldehydes, ketones, mineral oil, higher alcohols, finely divided organic and inorganic solid materials. In addition to the above-mentioned liquid hydrocarbons, the carrier can contain conventional emulsifying agents which can be used for causing the acetal compound to be dispersed in, and diluted with, water for end-use application. Still other liquid carriers can include organic solvents such as aliphatic and aromatic alcohols, esters, aldehydes, and ketones. Aliphatic monohydric alcohols include methyl, ethyl, normal-propyl, isopropyl, normal-butyl, sec-butyl, and tert-butyl alcohols. Suitable alcohols include glycols (such as ethylene and propylene glycol) and pinacols. Suitable polyhydroxy alcohols include glycerol, arabitol, erythritol, sorbitol, and the like. Finally, suitable cyclic alcohols include cyclopentyl and cyclohexyl alcohols.

Conventional aromatic and aliphatic esters, aldehydes and ketones can be used as carriers, and occasionally are used in combination with the above-mentioned alcohols. Still other liquid carriers include relatively high-boiling petroleum products such as mineral oil and higher alcohols (such as cetyl alcohol). Additionally, conventional or so-called "stabilizers" (e.g. tert-butyl sulfinyl dimethyl dithiocarbonate) can be used in conjunction with, or as a component of, the carrier or carriers used in a composition as made according to this invention.

Numerous clays having a layered structure with interstices, and synthetic inorganic materials that resemble such clays in respect of chemical composition, crystallinity and layered morphology, are suitable for use herein as carriers. Suitable clays having a layered structure with interstices include smectite, kaolin, muscovite, vermiculite, phlogopite, xanthophyllite, and chrysotile, and mixtures thereof. Preferred are smectite clays and kaolin clays. Smectite clays include montmorillonite, beidellite, nontronite, saponite, hectorite, sauconite, and others. Kaolin clays include kaolinite, deckite, nacrite, antigorite, and others. Most preferred is montmorillonite. Average particle sizes range from 0.5 to 50 micrometers.

Desirable properties of a topical composition or article repellent to insects and/or arthropods include low toxicity, resistance to loss by water immersion or sweating, low or no odor or at least a pleasant odor, ease of application, and rapid formation of a dry tack-free surface film on the host's skin or other surface. In order to obtain these properties, the formulation for a topical repellent or repellant article should permit animals infested with insects and/or arthropods (e.g. dogs with fleas, poultry with lice, cows with horn flies or ticks, and humans) to be treated with a repellent (including a composition thereof) by contacting the skin, hide, hair, fur or feathers of such human or animal with an effective amount of the repellent for repelling the insect or arthropod from the human or animal host.

The application of an effective amount of an repellant composition on a surface subject to attack by insects (such as skin, hide, hair, fur or feathers; or a plant or crop surface; or a container or packaging material) may be accomplished by dispersing the repellent into the air or dispersing the repellent as a liquid mist or incorporated into a powder or dust, and this will permit the repellent to fall on the desired host surfaces. It may also be desirable to formulate a repellent by combining an acetal compound to form a composition with a fugitive vehicle for application in the form of a spray. Such a composition may be an aerosol, sprayable liquid or sprayable powder composition adapted to disperse the active compound into the atmosphere by means of a compressed gas, or a mechanical pump spray. Likewise, directly spreading of a liquid/semi-solid/solid repellent on the host in wet or dry form (as a friable solid, for example) is an effective method of contacting the surface of the host with an effective amount of the repellent.

Further, it may also be desirable to combine one or more of the active compounds described herein with one or more other compounds known to have insect repellency in a composition to achieve the synergistic effect as may result from such a combination. Suitable compounds known for insect repellency combinable for such purpose include but are not limited to dihydronepetalactone, a nepetalactam, a dihydronepetalactam, benzil, benzyl benzoate, 2,3,4,5-bis(butyl-2-ene)tetrahydrofurfural, butoxypolypropylene glycol, N-butylacetanilide, normal-butyl-6,6-dimethyl-5,6-dihydro-1,4-pyrone-2-carboxylate, dibutyl adipate, dibutyl phthalate, di-normal-butyl succinate, N,N-diethyl-meta-toluamide, dimethyl carbate, dimethyl phthalate, 2-ethyl-2-butyl-1,3-propanediol, 2-ethyl-1,3-hexanediol, di-normal-propyl isocinchomeronate, 2-phenylcyclohexanol, p-methane-3,8-diol, and normal-propyl N,N-diethylsuccinamate.

In addition to one or more of the active compounds described herein, an insect repellent composition may also include one or more essential oils and/or active ingredients of essential oils. "Essential oils" are defined as any class of volatile oils obtained from plants possessing the odor and other characteristic properties of the plant. Examples of useful essential oils include: almond bitter oil, anise oil, basil oil, bay oil, caraway oil, cardamom oil, cedar oil, celery oil, chamomile oil, cinnamon oil, citronella oil, clove oil, coriander oil, cumin oil, dill oil, eucalyptus oil, fennel oil, ginger oil, grapefruit oil, lemon oil, lime oil, mint oil, parsley oil, peppermint oil, pepper oil, rose oil, spearmint oil (menthol), sweet orange oil, thyme oil, turmeric oil, and oil of wintergreen. Examples of active ingredients in essential oils are: citronellal, methyl salicylate, ethyl salicylate, propyl salicylate, citronellol, safrole, and limonene.

The insects and arthropods that may be repelled by the compounds and/or compositions of this invention may include any member of a large group of invertebrate animals characterized, in the adult state (non-adult insect states include larva and pupa) by division of the body into head, thorax, and abdomen, three pairs of legs, and, often (but not always) two pairs of membranous wings. This definition therefore includes a variety of biting insects (e.g. ants, bees, chiggers, fleas, mosquitoes, ticks, wasps), biting flies [e.g. black flies, green head flies, stable flies, horn flies (*haematobia irritans*)], wood-boring insects (e.g. termites), noxious insects (e.g. houseflies, cockroaches, lice, roaches, wood lice), and household pests (e.g. flour and bean beetles, dust mites, moths, silverfish, weevils).

A host from which it may be desired to repel an insect may include any plant or animal (including humans) affected by insects. Typically, hosts are considered to be insect-acceptable food sources or insect-acceptable habitats. For example, humans and animals serve as food source hosts for blood-feeding insects and arthropods such as biting flies, chiggers, fleas, mosquitoes, ticks and lice. In other embodiments of the invention, however, harvested, milled or refined grain, or other stored food products, which may be held in a paper, plastic or textile container, may be a desirable target and thus serve as a host for insects such as a weevil, flour or bean beetle, cockroach or silverfish.

In another embodiment, a compound of this invention may be used as a fragrance compound or as an active in a fragrance composition, and be applied in a topical manner to human or animal skin or hair to impart a pleasing fragrance, as in skin lotions and perfumes for humans or pets.

Particularly because of the pleasant aroma associated with the compounds hereof, a further embodiment of this invention is one in which one or more acetal compounds are formulated into a composition for use as a product that is directed to other fundamental purposes. The fragrance and/or insect repellency of these products will be enhanced by the presence therein of an active compound or composition of this invention. Such products include without limitation colognes, lotions, sprays, creams, gels, ointments, bath and shower gels, foam products (e.g. shaving foams), makeup, deodorants, shampoo, hair lacquers/hair rinses, and personal soap compositions (e.g. hand soaps and bath/shower soaps). The compound(s) may of course be incorporated into such products simply to impart a pleasing aroma. Any means of incorporation such as is practiced in the art is satisfactory.

A corresponding aspect of the wide variety of products discussed above is a further alternative embodiment of this invention, which is a process for fabricating a composition of matter, a topical treatment for skin, or an article of manufacture, by providing as the composition, or incorporating into the composition, skin treatment or article, one or more acetal compounds, or a mixture of stereoisomers thereof. Such products, and the method and process described above, illustrate the use of an acetal compound as a fragrance compound or perfume, or in a fragrance composition or formulation, or in a topical treatment for skin, or in an article of manufacture. In fabricating a composition of matter, for example, the composition could be prepared as a sprayable liquid, an aerosol, a foam, a cream, an ointment, a gel, a paste, a powder or a friable solid. The process of fabrication in such case would thus include admixing an active with suitable carriers or other inert ingredients to facilitate delivery in the physical form as described, such as liquid carriers that are readily sprayed; a propellant for an aerosol or a foam; viscous carriers for a cream, an ointment, a gel or a paste; or dry or semi-solid carriers for a powder or a friable solid.

A composition containing one or more of the above described active compounds prepared as an insect/arthropod repellent, fragrance product, skin treatment or other personal care product may also contain other therapeutically or cosmetically active adjuvants or supplemental ingredients as are typical in the personal care industry. Examples of these include fungicides, sunscreening agents, sunblocking agents, vitamins, tanning agents, plant extracts, anti-inflammatory agents, anti-oxidants, radical scavenging agents, retinoids, alpha-hydroxy acids, antiseptics, antibiotics, antibacterial agents, antihistamines; adjuvants such as thickeners, buffering agents, chelating agents, preservatives, gelling agents, stabilizers, surfactants, emollients, coloring agents, aloe vera, waxes, and penetration enhancers; and mixtures of any two or more thereof.

In a further embodiment of this invention, an acetal compound is incorporated into an article to produce an insect/arthropod repellent effect. Articles contemplated to fall within this embodiment include manufactured goods, including textile goods such as clothing, outdoor or military equipment such as mosquito netting; natural products such as lumber or the leaves of insect vulnerable plants; or packaging material such as that made from paper, cardboard, plastic or fabric, as may be used in containers such as bags, boxes or barrels. The active may be incorporated into or onto the surface of the article by a method such as spraying or coating the active or a formulation thereof, or by dipping the article in a bath of the active or a formulation thereof.

In another embodiment of this invention, an acetal compound is incorporated into an article to produce a fragrance pleasing to humans, or an acetal compound is applied to the surface of an object to impart an odor thereto. The particular manner of application will depend upon the surface in question and the concentration required to impart the necessary intensity of odor. Articles contemplated to fall within these embodiments include manufactured goods, including textile goods, air fresheners, candles, various scented articles, fibers, sheets, paper, paint, ink, clay, wood, furniture (e.g. for patios and decks), carpets, sanitary goods, plastics, polymers, and the like.

An acetal compound may be admixed in a composition with other components, such as a carrier, in an amount that is effective for usage for a particular purpose, such as an insect/arthropod repellant, fragrance or other skin treatment. The amount of the active compound contained in a composition will generally not exceed about 80% by weight based on the weight of the final product, however, greater amounts may be utilized in certain applications, and this amount is not limiting. More preferably, a suitable amount of the compound will be at least about 0.001% by weight and preferably about 0.01% up to about 50% by weight; and more preferably, from about 0.01% to about 20% weight percent, based on the total weight of the total composition or article. Specific compositions will depend on the intended use.

Other methods of using an acetal compound are as disclosed in US 2003/062,357; US 2003/079,786; and US 2003/191,047, each of which is incorporated in its entirety as a part hereof.

The present invention is further described in, but not limited by, the following specific embodiments.

EXAMPLES

General Procedures

All reactions and manipulations related to the synthesis of the control and test repellents were carried out in a standard laboratory fume hood in standard laboratory glassware. Nepetalactone (II), consisting mainly of the cis,trans-stereoisomer, was obtained by steam distillation of commercially-available catnip oil from *Nepeta cataria*, obtained from Berjé, (Bloomfield, N.J.). All inorganic salts and organic solvents, with the exception of anhydrous THF, were obtained from VWR Scientific (West Chester, Pa.). All other reagents used in the examples were obtained from Sigma-Aldrich Chemical (Milwaukee, Wis.) and used as received. The acetal products were characterized by NMR spectroscopy. NMR spectra were obtained on a Bruker DRX Advance (500 MHz $^1$H, 125 MHz $^{13}$C; Bruker Biospin Corp., Billerica, Mass.) using deuterated solvents obtained from Cambridge Isotope Laboratories, Inc. (Andover, Mass.).

The meaning of abbreviations used is as follows: "mL" means milliliter(s), "µL" means microliter, "g" means gram(s), "mg" means milligram, "psi" means pounds per square inch, "MP" means melting point, "NMR" means nuclear magnetic resonance, "° C." means degrees Centigrade.

The nepetalic acid employed in Examples 1-6 was prepared according to the following procedures, although there was some variation in the amounts employed from batch to batch. A solution of cis-trans nepetalactone in 5 mL of tetrahydrofuran (THF) was treated with sodium hydroxide (1.0 g in 5 (mL of water) resulting in initially a two-phase mixture and then yellow solution. After 1 hour, the basic solution was extracted twice with fresh 20 mL aliquots of ethyl acetate. The aqueous layer from this extraction was acidified with 1N HCl drop-wise to pH=3 at which point it turned into a white heterogeneous mixture. The thus formed aqueous mixture was extracted twice with ethyl acetate and dried over anhydrous sodium sulfate. Removal of the solvent under vacuum resulted in a yellow oil which was triturated with petroleum ether (100 mL) and allowed to crystallize to a white solid on standing. The white solid was filtered, washed with cold petroleum ether (20 mL) and dried under high vacuum to afford nepetalic acid (1.9 g, 69%) with a melting point of 67° C. (71° C. in *J. Org. Chem.*, Vol. 46, No. 16, 1981, pp. 3302-3305).

Example 1

Methyl Acetal of Nepetalic Acid

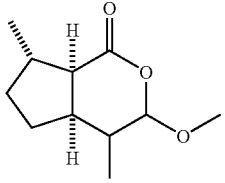

(4aR,7S,7aR)-3-methoxy-4,7-dimethylhexahydrocyclopenta[c]pyran-1(3H)-one

Nepetalic acid derived from 7S-configured cis,trans-nepetalactone is dissolved in methanol and stirred at room temperature overnight. Removal of the solvent under reduced pressure afforded the methyl acetal of nepetalic acid. NMR analysis of the product obtained indicated the acetal product obtained was a mixture of diastereomers. GC/MS analysis showed the acetal product thermally reverting to nepetalactone.

Example 2

Ethyl Acetal of Nepetalic Acid

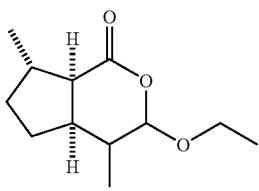

(4aR,7S,7aR)-3-ethoxy-4,7-dimethylhexahydrocyclopenta[c]pyran-1(3H)-one

Nepetalic acid derived from 7S-configured cis,trans-nepetalactone is dissolved in ethanol and stirred at room temperature overnight. Removal of the solvent under reduced pressure afforded the ethyl acetal of nepetalic acid. NMR analysis of the product obtained indicated the acetal product obtained was a mixture of diastereomers. GC/MS analysis showed the acetal product thermally reverting to nepetalactone.

Example 3 n-Propyl Acetal of Nepetalic Acid

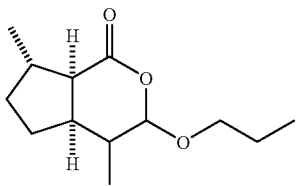

(4aR,7S,7aR)-3-n-propoxy-4,7-dimethylhexahydrocyclopenta[c]pyran-1(3H)-one

Nepetalic acid derived from 7S-configured cis,trans-nepetalactone is dissolved in n-propanol and stirred at room temperature overnight. Removal of the solvent under reduced pressure afforded the n-propyl acetal of nepetalic acid. NMR analysis of the product obtained indicated the acetal product obtained was a mixture of diastereomers. GC/MS analysis showed the acetal product thermally reverting to nepetalactone.

Example 4

Isopropyl Acetal of Nepetalic Acid

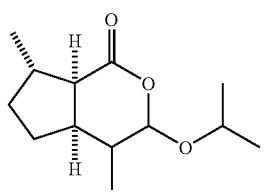

(4aR,7S,7aR)-3-isopropoxy-4,7-dimethylhexahydrocyclopenta[c]pyran-1(3H)-one

Nepetalic acid derived from 7S-configured cis,trans-nepetalactone is dissolved in isopropanol and stirred at room temperature overnight. Removal of the solvent under reduced pressure afforded the isopropyl acetal of nepetalic acid. NMR analysis of the product obtained indicated the acetal product obtained was a mixture of diastereomers. GC/MS analysis showed the acetal product thermally reverting to nepetalactone.

Example 5 n-Butyl Acetal of Nepetalic Acid

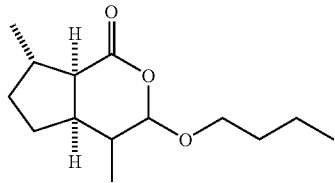

(4aR,7S,7aR)-3-n-butoxy-4,7-dimethylhexahydrocyclopenta[c]pyran-1(3H)-one

Nepetalic acid derived from 7S-configured cis,trans-nepetalactone is dissolved in n-butanol and stirred at room temperature overnight. Removal of the solvent under reduced pressure afforded the n-butyl acetal of nepetalic acid. NMR analysis of the product obtained indicated the acetal product obtained was a mixture of diastereomers. GC/MS analysis showed the acetal product thermally reverting to nepetalactone.

Example 6

Iso-Butylacetal of Nepetalic Acid

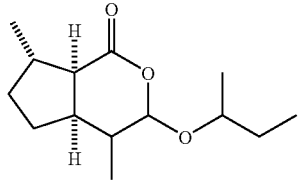

(4aR,7S,7aR)-3-isobutoxy-4,7-dimethylhexahydro-cyclopenta[c]pyran-1(3H)-one

Nepetalic acid derived from 7S-configured cis,trans-nepetalactone is dissolved in isobutanol and stirred at room temperature overnight. Removal of the solvent under reduced pressure afforded the isobutyl acetal of nepetalic acid. NMR analysis of the product obtained indicated the acetal product obtained was a mixture of diastereomers. GC/MS analysis showed the acetal product thermally reverting to nepetalactone.

Example 7

In Vitro Insect Repellency of the Nepetalic Acid Acetals of Examples 1-6

The products of Examples 1-6 were evaluated for the insect repellency against *Aedes aegypti* mosquitoes in the in vitro Gupta box landing assay. In this method, a chamber contained 5 wells, each covered by a Baudruche (animal intestine) membrane. Each well was filled with bovine blood, containing sodium citrate (to prevent clotting) and ATP (72 mg ATP disodium salt per 26 ml of blood), and heated to 37° C. A volume of 25 µl of isopropyl alcohol(IPA) containing one test specimen, or DEET as a control, was applied to each membrane. The concentrations were all 1% w/v in IPA except where otherwise indicated. The control was a membrane surface treated with a 1% solution of DEET.

After 5 min, approximately 250 4-day-old female *Aedes aegypti* mosquitoes were introduced into the chamber. The number of mosquitoes probing the membranes for each treatment was recorded at 2 min intervals over 20 min. Each datum represents the mean of three replicate experiments.

From these data, the % mean repellency for a repellent at a given concentration of repellent test solution was determined using the following equation:

% mean repellency=$(C-T)/C \times 100$ where

C=the total number of landings on the IPA control well, and
T=the total number of landings on the test solution well.

The % mean repellencies at 1% (w/v) are depicted in Table 2 in addition to mean time to first landing, and mean number of total landings for the nepetalic acid acetals of Examples 1-6 and for DEET as a control.

TABLE 2

| Acetal R group | Example Number | % Mean repellency | Mean time to first landing (min) | Mean number of total landings |
|---|---|---|---|---|
| methyl | 1 | 79.30 | 3.2 | 12.2 |
| ethyl | 2 | 52.40 | 5.2 | 26.4 |
| n-propyl | 3 | 89.10 | 11.6 | 5.2 |
| n-butyl | 4 | 73.20 | 2.8 | 30.6 |
| i-propyl | 5 | 17.80 | 2.8 | 33.8 |
| i-butyl | 6 | 20.40 | 2.0 | 91.6 |
| DEET | Control | 68.60 | 3.5 | 17.7 |

Certain features of this invention are described herein in the context of an embodiment that combines various such features together, whether as described in the disclosure or in one of the drawings. The scope of the invention is not, however, limited by the description of only certain features within any particular embodiment, and the invention also includes (1) a subcombination of fewer than all of the features of any described embodiment, which subcombination may be characterized by the absence of the features omitted to form the subcombination; (2) each of the features, individually, included within the combination of the described embodiment; and (3) other combinations of features formed from one or more or all of the features of the described embodiment together with other features as disclosed elsewhere herein.

What is claimed is:

1. A compound represented generally by the following schematic formula:

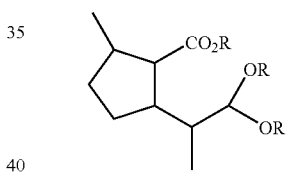

which is S configured at the methyl-bearing carbon on the cyclopentyl ring, and wherein R comprises (a) an alkane radical, (b) an alkene radical, (c) an alkyne radical, or (d) an aromatic radical.

2. A compound according to claim 1 wherein R is derived from
   (a) a $C_1$ to $C_{20}$ straight-chain, branched or cyclic alkane or alkene radical, which optionally includes one or more heteroatoms selected from the group consisting of O, N and S, and/or optionally includes a substituent derived from a $C_6$ to $C_{20}$ aromatic radical; or
   (b) a $C_6$ to $C_{20}$ aromatic radical, which optionally (i) is substituted with a $C_1$ to $C_{12}$ straight-chain, branched or cyclic alkane or alkene radical (itself being optionally substituted with Cl, Br or F); and/or (ii) is substituted with a halogen selected from the group consisting of Cl, Br and F; and/or (iii) comprises one or more heteroatoms selected from the group consisting of O, N and S.

3. A compound according to claim 1 wherein R is selected from the group consisting of methyl, ethyl, n-propyl, i-propyl, n-butyl, t-butyl, n-pentyl, n-hexyl, cyclohexyl, n-octyl, trimethylpentyl, cyclooctyl, allyl, propargyl, phenyl, methylphenyl, ethylphenyl, n-propylphenyl, n-butylphenyl, t-butylphenyl, p-chlorophenyl, p-bromophenyl, naphthyl and ethyl naphthyl.

4. A compound according to claim 1 which is a single stereoisomer of a single compound, or is a mixture of stereoisomers of a single compound.

5. A compound represented generally by the following schematic formula:

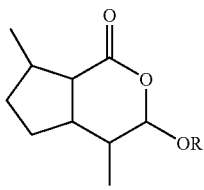

which is S configured at the methyl-bearing carbon on the cyclopentyl ring, and wherein R comprises (a) an alkane radical, (b) an alkene radical, (c) an alkyne radical, or (d) an aromatic radical.

6. A compound according to claim 5 wherein R is derived from
(a) a $C_1$ to $C_{20}$ straight-chain, branched or cyclic alkane or alkene radical, which optionally includes one or more heteroatoms selected from the group consisting of O, N and S, and/or optionally includes a substituent derived from a $C_6$ to $C_{20}$ aromatic radical; or
(b) a $C_6$ to $C_{20}$ aromatic radical, which optionally (i) is substituted with a $C_1$ to $C_{12}$ straight-chain, branched or cyclic alkane or alkene radical (itself being optionally substituted with Cl, Br or F); and/or (ii) is substituted with a halogen selected from the group consisting of Cl, Br and F; and/or (iii) comprises one or more heteroatoms selected from the group consisting of O, N and S.

7. A compound according to claim 5 wherein R is selected from the group consisting of methyl, ethyl, n-propyl, i-propyl, n-butyl, t-butyl, n-pentyl, n-hexyl, cyclohexyl, n-octyl, trimethylpentyl, cyclooctyl, allyl, propargyl, phenyl, methylphenyl, ethylphenyl, n-propylphenyl, n-butylphenyl, t-butylphenyl, p-chlorophenyl, p-bromophenyl, naphthyl and ethyl naphthyl.

8. A compound according to claim 5 which is a single stereoisomer of a single compound, or is a mixture of stereoisomers of a single compound.

9. A process for preparing a nepetalic acid acetal comprising contacting a nepetalic acid with an alcohol.

10. A process according to claim 9 which proceeds generally according to a reaction scheme as described in Equation 4

Equation 4

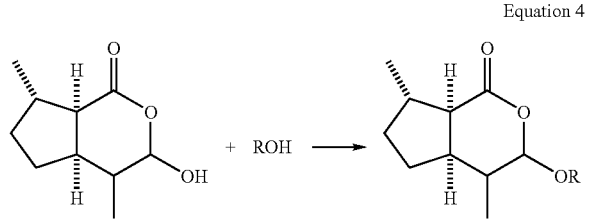

wherein R comprises (a) an alkane radical, (b) an alkene radical, (c) an alkyne radical, or (d) an aromatic radical.

11. A process according to claim 9 which proceeds generally according to a reaction scheme as described in Equation 5

Equation 5

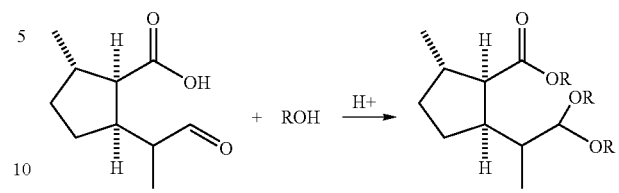

wherein R comprises (a) an alkane radical, (b) an alkene radical, (c) an alkyne radical, or (d) an aromatic radical.

12. A composition of matter comprising (a) one or both of (i) a compound represented generally by the following schematic formula:

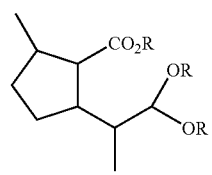

wherein R comprises (A) an alkane radical, (B) an alkene radical, (C) an alkyne radical, or (D) an aromatic radical; and (ii) a compound represented generally by the following schematic formula:

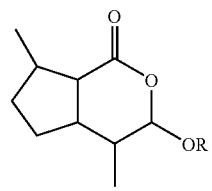

wherein R comprises (A) an alkane radical, (B) an alkene radical, (C) an alkyne radical, or (D) an aromatic radical; and (b) one or both of (i) a carrier to adjust the concentration of the compound within the composition, and (ii) a cosmetic adjuvant.

13. A composition according to claim 12 wherein an adjuvant is selected from any one or more members of the group consisting of a fungicide, sunscreening agent, sunblocking agent, vitamin, tanning agent, plant extract, anti-inflammatory agent, anti-oxidant, radical scavenging agent, retinoid, alpha-hydroxy acid, antiseptic, antibiotic, antibacterial agent, antihistamine, thickener, buffering agent, chelating agent, preservative, gelling agent, stabilizer, surfactant, emollient, coloring agent, aloe vera, wax, and penetration enhancer.

14. The composition of claim 12 which comprises the compound in an amount of from about 0.01% to about 20% by weight of the total weight of the composition.

15. The composition of claim 12 in the form of a sprayable liquid, an aerosol, a foam, a cream, an ointment, a gel, a paste, a powder or a friable solid.

16. A method for repelling an insect or arthropod comprising exposing the insect or arthropod to one or both of (a) a compound represented generally by the following schematic formula:

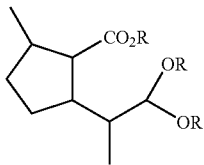

wherein R comprises (i) an alkane radical, (ii) an alkene radical, (iii) an alkyne radical, or (iv) an aromatic radical; and (b) a compound represented generally by the following schematic formula:

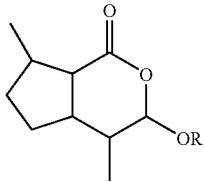

wherein R comprises (i) an alkane radical, (ii) an alkene radical, (iii) an alkyne radical, or (iv) an aromatic radical.

17. A method according to claim 16 which comprises exposing an insect or arthropod to compound(s) that are in the form of a sprayable liquid, an aerosol, a foam, a cream, an ointment, a gel, a paste, a powder or a friable solid.

18. A method according to claim 16 which comprises applying compound(s) to the skin, hide, hair, feathers or fur of a human or animal host for an insect or arthropod.

19. A method according to claim 16 which comprises exposing an insect or arthropod selected from the group consisting of biting flies, chiggers, fleas, mosquitoes, ticks, lice, weevils, flour beetles, bean beetles, roaches and silverfish to compound(s).

20. An article of manufacture that comprises one or both of (a) a compound represented generally by the following schematic formula:

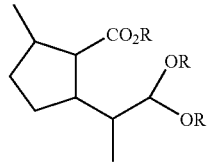

wherein R comprises (i) an alkane radical, (ii) an alkene radical, (iii) an alkyne radical, or (iv) an aromatic radical; and (b) a compound represented generally by the following schematic formula:

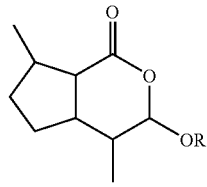

wherein R comprises (i) an alkane radical, (ii) an alkene radical, (iii) an alkyne radical, or (iv) an aromatic radical.

* * * * *